United States Patent (12)
Gordon et al.

(10) Patent No.: US 9,440,086 B2
(45) Date of Patent: Sep. 13, 2016

(54) OPTIMIZED FLASH MEMORY DEVICE FOR MINIATURIZED DEVICES

(71) Applicant: MEDTRONIC, INC., Minneapolis, MN (US)

(72) Inventors: Charles R. Gordon, Phoenix, AZ (US); Duane R. Bigelow, Gilbert, AZ (US)

(73) Assignee: Medtronic, Inc., Minneapolis, MN (US)

(*) Notice: Subject to any disclaimer, the term of this patent is extended or adjusted under 35 U.S.C. 154(b) by 171 days.

(21) Appl. No.: 14/059,544

(22) Filed: Oct. 22, 2013

(65) Prior Publication Data
US 2015/0073497 A1 Mar. 12, 2015

Related U.S. Application Data

(60) Provisional application No. 61/876,431, filed on Sep. 19, 2013.

(51) Int. Cl.
*G06F 1/32* (2006.01)
*A61N 1/37* (2006.01)
*A61N 1/372* (2006.01)
*A61N 1/36* (2006.01)
*G06F 9/445* (2006.01)

(52) U.S. Cl.
CPC .............. *A61N 1/37264* (2013.01); *A61N 1/36* (2013.01); *G06F 8/665* (2013.01); *G06F 9/445* (2013.01)

(58) Field of Classification Search
CPC .............. A61N 1/3708; A61N 1/3782; A61N 1/3975; H04J 3/06; G06F 1/32–1/3296
See application file for complete search history.

(56) References Cited

U.S. PATENT DOCUMENTS

| | | | |
|---|---|---|---|
| 4,374,382 A | 2/1983 | Markowitz | |
| 4,556,063 A | 12/1985 | Thompson et al. | |
| 5,052,388 A | 10/1991 | Sivula et al. | |
| 5,127,404 A | 7/1992 | Wyborny et al. | |
| 5,987,352 A | 11/1999 | Klein et al. | |
| 6,026,465 A * | 2/2000 | Mills ................... | G06F 12/0607 711/103 |
| 6,184,726 B1 * | 2/2001 | Haeberli ................ | G11C 5/145 327/307 |
| 6,195,290 B1 | 2/2001 | Dallabora et al. | |
| 6,241,704 B1 | 6/2001 | Peterson et al. | |
| 6,721,843 B1 | 4/2004 | Estakhri | |
| 7,702,885 B2 | 4/2010 | Cohen | |
| 7,804,713 B2 | 9/2010 | Parker | |
| 8,085,616 B2 | 12/2011 | Ryu | |

(Continued)

FOREIGN PATENT DOCUMENTS

WO WO 2007/050338 A1 5/2007

OTHER PUBLICATIONS

Walsh, et al., "Memory Array with Flash and Random Access Memory and Method Therefor", U.S. Appl. No. 13/663,099, filed Oct. 29, 2012, 22 pages.

(Continued)

*Primary Examiner* — Christopher D Koharski
*Assistant Examiner* — Natasha Patel
(74) *Attorney, Agent, or Firm* — Evans M. Mburu

(57) ABSTRACT

An implantable medical device have an associated memory device is disclosed. The implantable medical device utilizes techniques for optimizing one or more embedded operations of the memory device, such operations including programming, reading or erasing data. The techniques for optimizing the embedded operations include controlling the operations as a function of an energy source of the implantable medical device.

17 Claims, 6 Drawing Sheets

(56) References Cited

U.S. PATENT DOCUMENTS

| | | | |
|---|---|---|---|
| 8,391,068 B2 | 3/2013 | Shelton et al. | |
| 8,462,558 B2 | 6/2013 | Moon et al. | |
| 8,462,564 B1 | 6/2013 | Wu et al. | |
| 8,683,249 B2 * | 3/2014 | Kanai | G06F 1/3275 |
| | | | 713/323 |
| 2007/0060955 A1 | 3/2007 | Strother et al. | |
| 2007/0091687 A1 * | 4/2007 | Armstrong | A61N 1/37264 |
| | | | 365/185.29 |
| 2007/0208261 A1 | 9/2007 | Maniak et al. | |
| 2008/0024899 A1 * | 1/2008 | Chu | G06F 3/0614 |
| | | | 360/69 |
| 2010/0023682 A1 * | 1/2010 | Lee | G06F 12/0246 |
| | | | 711/103 |
| 2010/0302861 A1 * | 12/2010 | Moon | G11C 16/3404 |
| | | | 365/185.19 |
| 2012/0221801 A1 * | 8/2012 | Okawa | G06F 1/3212 |
| | | | 711/154 |
| 2012/0239868 A1 | 9/2012 | Ryan et al. | |
| 2012/0324274 A1 * | 12/2012 | Hori | G06F 1/30 |
| | | | 714/6.1 |
| 2013/0035737 A1 * | 2/2013 | Ryu | A61N 1/3682 |
| | | | 607/25 |

OTHER PUBLICATIONS (PCT/US2014/054667) PCT Notification of Transmittal of the International Search Report and the Written Opinion of the International Searching Authority.

* cited by examiner

OPTIMIZED FLASH MEMORY DEVICE FOR MINIATURIZED DEVICES

CROSS-REFERENCE TO RELATED APPLICATION

This application claims priority to provisional U.S. Application No. 61/876,431, filed Sep. 11, 2013, which is incorporated herein by reference in its entirety.

FIELD

The present disclosure pertains to implantable medical devices and more particularly to implantable medical devices having memory devices with optimized embedded operations.

BACKGROUND

There are a variety of medical devices that sense data, provide diagnostic information, and/or deliver therapy. When such a device is implanted (in whole or in part), it is referred to as an implantable medical device (IMD). Examples of IMDs are implantable loop recorders, implantable pacemakers, and implantable cardioverter-defibrillators, which are electronic medical devices that monitor the electrical activity of the heart and/or provide electrical stimulation to one or more of the heart chambers, when necessary.

As IMD technology advances in an attempt to address a myriad of life sustaining/enhancing needs, issues such as IMD battery longevity, IMD mass, and increased functionality remain key considerations in the IMD design process. A conventional approach to providing power within an IMD involves the use of a self-contained battery, not unlike a common battery which is commercially available to the consumer. Such a self-contained battery includes active electrochemical cell components housed in a battery can. Battery housing connectors or contacts are provided for establishing electrical connections to circuitry disposed within the IMD.

The functions attributable to the IMD may be impacted by the depletion of the battery energy. For example, each IMD generally includes a processor that executes "operation instructions" or applies "operation code" to carry out the various operational functions of the IMD. Typical operation instructions are stored in one or more non-volatile memory modules in the IMD. In addition, data sensed by the IMD is stored in the one or more volatile memory modules. Non-volatile memory includes, for example, flash memory, read-only memory (ROM), electrically erasable programmable read-only memory (EEPROM), and a non-volatile random-access memory (NVRAM).

Much attention has been placed on optimizing the functions of the IMD to optimize consumption of the power source of an implantable medical device. The battery consumption is always a concern when designing implantable medical devices, but this concern is increased for small form factor devices that can only accommodate a small battery canister. There remains a need for increased optimization of the operational functions of the IMD pertaining to the storage operations in the volatile memory modules.

SUMMARY

Generally, the disclosure is directed to the design of one or more memory devices within an implantable medical device (IMD). In accordance with aspects of the present invention, techniques are disclosed for implementing a memory device with a programming delay enables the downsizing of the battery size and capacity of the IMD.

In one aspect, an implantable medical device including a battery, a processing unit, and a memory device is disclosed. The memory device includes a memory sector including a plurality of memory elements, and a state machine that is configured to control a timing associated with a programming operation of the memory sector as a function of a parameter of the battery.

The programming operation may be controlled by varying a timing of writing of data to a given memory element of the memory sector as a function of a programming delay duration following a preceding writing of data to a first memory element.

In another aspect, a method of programming a memory device of an implantable medical device is disclosed. The method includes the tasks of computing a parameter of a battery of the implantable medical device, erasing a memory sector of the memory device, performing an iterative programming of a plurality of elements in the memory sector, and applying a programming delay prior to programming at least one of the plurality of elements, wherein the programming delay is a function of the computed parameter.

In an embodiment, a value of the programming delay is defined as a function of the parameter of the battery.

The details of one or more examples are set forth in the accompanying drawings and the description below. Other features, objects, and advantages of the disclosure will be apparent from the description and drawings, and from the claims.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

Figure 1:
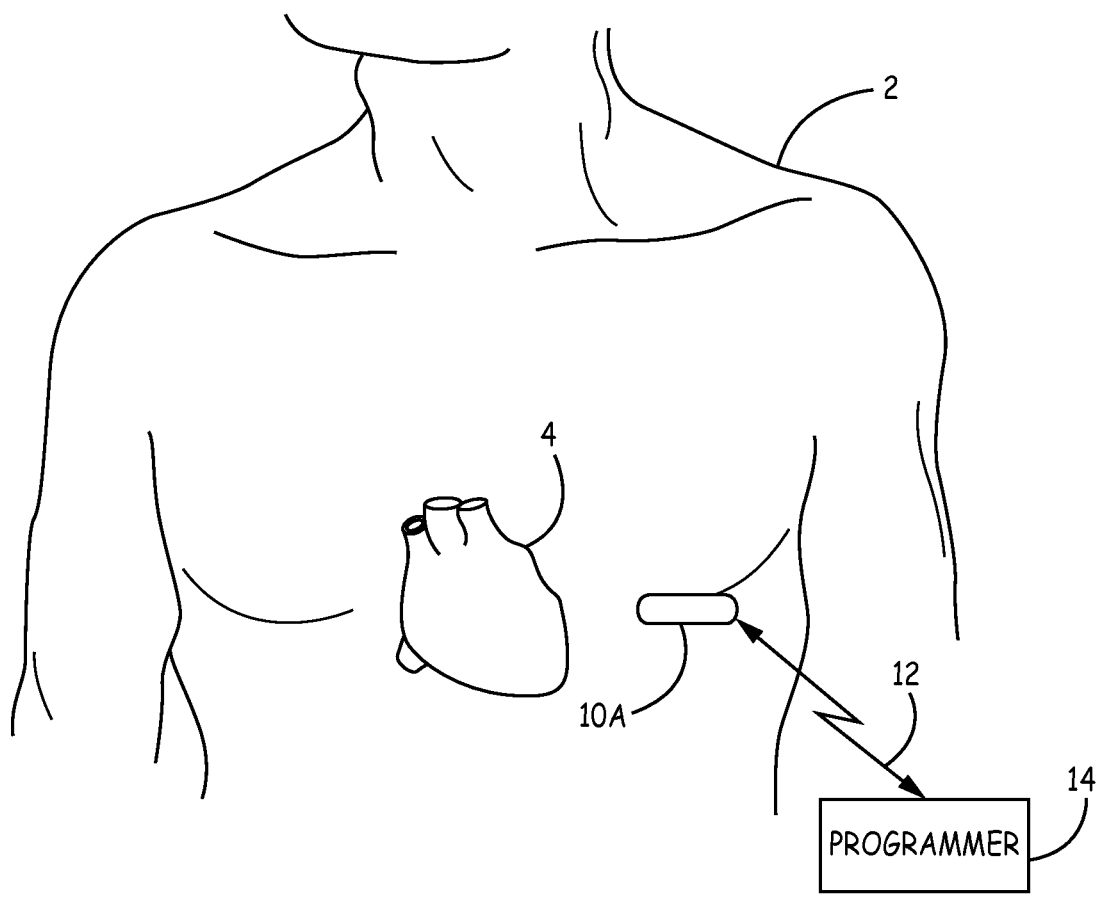
FIG. 1 is a conceptual diagram of a therapy system illustrating a frontal view of a patient in whom an implantable medical device may be implanted.

The present invention relates to configuration of flash memory devices to optimize power consumption of battery-powered devices such as implantable medical devices. As is generally known in the art, flash memory devices are a class of non-volatile memory devices. A flash memory device offers non-volatile storage of data, and also conveniently allows the data to be programmed (written) into the memory and erased from the memory multiple times, thus allowing a multitude of flexible applications. Such flash memory devices provide electrical erasing and a small cell size. In a flash memory device, a plurality of one-transistor core cells may be formed on a semiconductor substrate in which each cell is comprised of a P-type conductivity substrate, an N-type conductivity source region formed integrally with the substrate, and an N-type conductivity drain region also formed integrally within the substrate. A floating gate is separated from the substrate by a thin dielectric layer. A second dielectric layer separates a control gate from the floating gate. A P-type channel region in the substrate separates the source and drain regions.

One type of architecture used for flash memories is typically referred to as a NOR flash memory architecture which is an array of flash cells that are divided into a plurality of sectors. Further, the memory cells within each sector are assembled from memory elements that may comprise of multiple memory segments. A typical segment may include a few cells that make up a machine word (or byte) and each of the segments can be written or read independently.

In a typical NOR flash, the source region of each cell transistor within each sector is tied to a common node. Therefore, all of the cells within a particular sector can be erased simultaneously or erasure may be performed on a sector-by-sector basis. In order to program the flash cell, the drain region and the control gate are raised to predetermined potentials above the potential applied to the source region. For example, the drain region has applied thereto a voltage $V_D$ of approximately +5.5 volts with the control gate $V_G$ having a voltage of approximately +9 volts applied thereto. These voltages produce "hot electrons" which are accelerated across the thin dielectric layer and onto the floating gate. The hot electron injection results in an increase of the floating gate threshold by approximately two to four volts. To avoid unnecessarily obfuscating the novel aspects of the present invention, known details of operations of flash memory devices will not be described herein. The reader is referred to the description of operations in U.S. Pat. No. 8,462,564, "Flash memory programming power reduction" to Yonggang et al., incorporated herein by reference in its entirety.

For erasing the data in a flash cell, a positive potential (e.g., +5 volts) is applied to the source region. The control gate is applied with a negative potential (e.g., −8 volts), and the drain region is allowed to float. A strong electric field develops between the floating gate and the source region, and a negative charge is extracted from the floating gate to the source region by way of Fowler-Nordheim tunneling.

A flash memory device performs all its embedded operations, including the programming or erasing, based on the generation and control of many design parameters, such as analog signals, maximum values, timings, etc. The embedded operations in a flash memory device are complex, especially with regard to the generation and control of parameters and require very fine control. These parameters have to be properly defined and, from time to time, updated in the various phases of the operation in order to have perfect control of the full operation. The values of these parameters may depend on information stored in a series of registers that are associated with these parameters.

The present invention describes an architecture which introduces a high level of configurability in the flash memory devices and associated design parameters of a flash memory device. In the present invention, a flash memory device is described having operations that are handled by a process that is implemented by program instructions that may be stored in a read-only memory (ROM) and executed by a microcontroller. For example, the microcontroller may issue instructions to initiate a program or erase operation to implement the corresponding program or erase flash memory operation. The instruction is interpreted by the flash memory device, and specific signals are then generated to control the flash memory device in order to perform the requested flash memory operation. All of the needed configurations for each parameter in each operation phase are obtained by loading the corresponding information (values) into the associated registers.

As used in this disclosure, the term "program" refers to the operation of writing data to a location of memory. The words program and write will be used interchangeably in this disclosure.

As used in this disclosure, the term "conditional delay" refers to a controllable duration of time that may be selected to delay successive operations of two memory elements. Such operations may include a programming operation or an erasing operation. For simplicity, this disclosure will refer to a programming delay, although it should be understood that the concepts can be applied to an erasing delay with minimal modification that is within the scope of those skilled in the art with the benefit of this disclosure.

To more particularly describe the features of the present invention, please refer to FIGS. 1 through 6A-B in conjunction with the discussion below.

FIG. 1 is a conceptual diagram of a therapy system illustrating a frontal view of a patient 2 in whom an IMD 10A may be implanted subcutaneously with a typical implant location referenced thereon (other implant locations may be utilized). The IMD 10A senses cardiac electrical activation signals via electrodes (not shown in FIG. 1) from heart 4. A communication link 12 allows 2-way telemetry communication between IMD 10A and an external device (typically a programmer) 14. Programmer 14 and communication link 12 suitable for use in the practice of the present invention are known. Known programmers typically communicate with an implanted device such as IMD 10A via a bi-directional radiofrequency telemetry link, so that the programmer 14 can transmit control commands and operational parameter values to be received by the IMD 10A, and so that the IMD 10A can communicate captured and stored diagnostic and operational data to the programmer 14. Programmers 14 believed to be suitable for the purposes of practicing the present invention include the Models 9790 and CareLink® programmers, commercially available from Medtronic, Inc., Minneapolis, Minn. Various telemetry systems for providing the necessary communications channels between programmer 14 and an IMD 10A have been developed and are well known in the art and are discussed, for example, in the following U.S. patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device".

Figure 2:
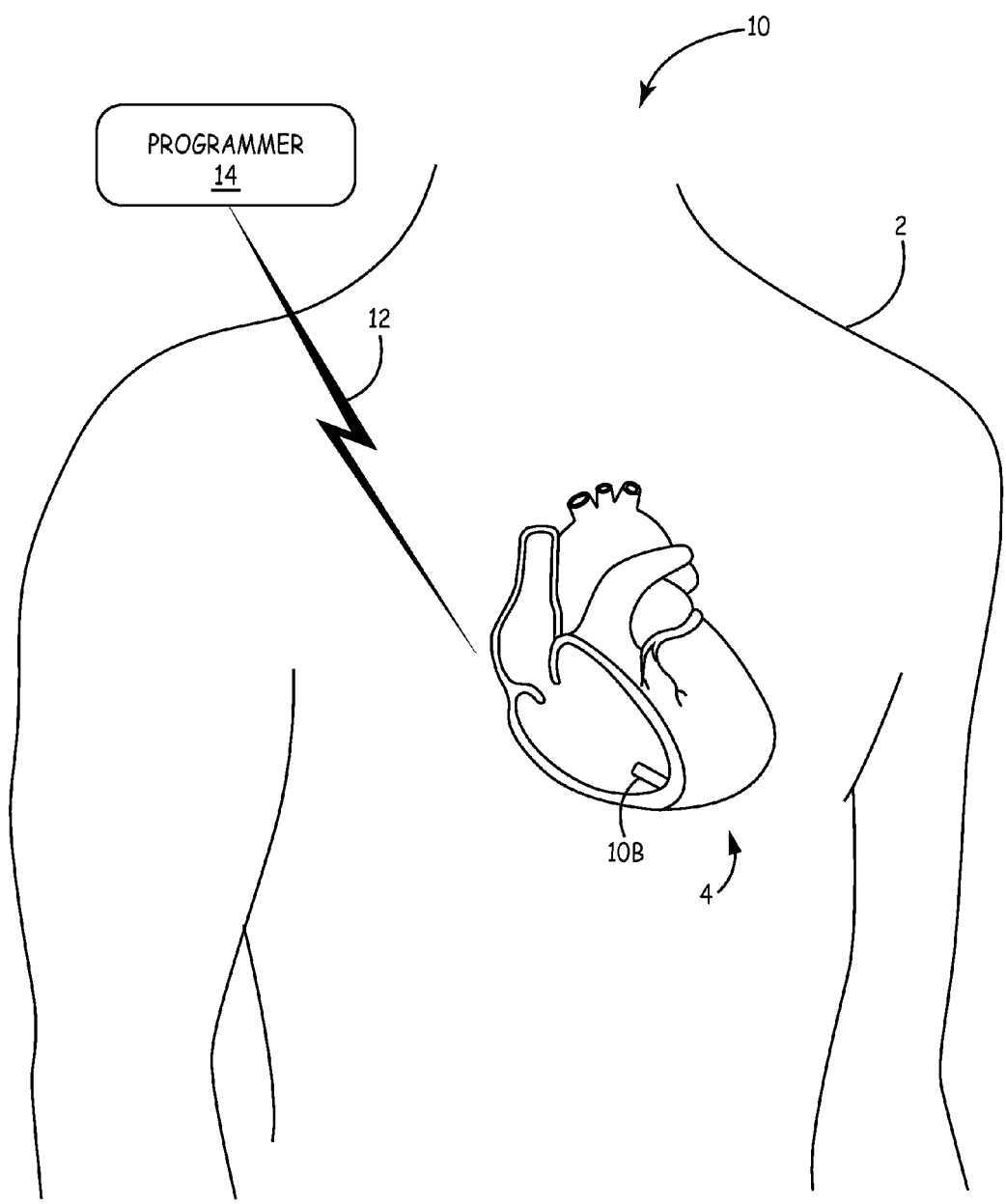
FIG. 2 illustrates another embodiment of a conceptual diagram of a therapy system having an implantable medical device implanted in a patient.

FIG. 2 illustrates another embodiment of a conceptual diagram of a therapy system having an IMD 10B that may be used to monitor one or more physiological parameters of patient 2 and/or to provide therapy to heart 4 of patient 2.

IMD 10B may be an implantable leadless pacemaker that provides stimulation therapy signals to heart 4 via one or more electrodes (not shown in FIG. 2) on its outer housing. In alternative embodiments, the IMD 10B may include one or more medical electrical leads (not shown) having electrodes for sensing and delivery electrical stimulation. Additionally or alternatively, IMD 10B may sense electrical signals attendant to the depolarization and repolarization of heart 4 via electrodes on its outer housing. In some examples, IMD 10B provides pacing pulses to heart 4 based on the electrical signals sensed within heart 4.

In the example of FIG. 2, IMD 10B is positioned wholly within heart 4 with one end proximate to the apex of right ventricle to provide right ventricular (RV) pacing. Although IMD 10B is shown within heart 4 and proximate to the apex of a right ventricle in the example of FIG. 2, IMD 10B may be positioned at any other location outside or within heart 4. For example, IMD 10B may be configured for implantation on an exterior wall of heart 4, or within a blood vessel in an alternative implementation. Depending in the location of implant, IMD 10B may include other stimulation functionalities. For example, IMD 10B may provide atrioventricular nodal stimulation, fat pad stimulation, vagal stimulation, or other types of neurostimulation. In other examples, IMD 10B may be a monitor that senses one or more parameters of heart 4 and may not provide any stimulation functionality.

Programmer 14 is depicted as being in communication with IMD 10B. As described above with respect to IMD 10A of FIG. 1, programmer 14 may also be used to communicate with IMD 10B. A user may use programmer 14 to retrieve information from IMD 10B regarding the performance of IMD 10B and to interact with programmer 14 to program, e.g., select parameters for, any additional therapies provided by IMD 10B. The programmer 14 also facilitates user interaction remotely via a networked computing device.

IMD 10A and 10B (collectively "IMD 10") may each include an internal power source such as a battery that supplies power to the components of the IMD 10 for achieving various functions of the IMD 10. With the advancements in the miniaturization of the implantable medical devices, such as IMD 10, the power source is also preferred to have a smaller footprint and hence decreased capacity for storage of energy. Therefore, the inventors of the present invention have observed that there is a need to optimize current consumption during the operation of the components of IMD 10. In particular, the inventors have disclosed herein techniques for optimizing operations of components associated with high current events, such as the embedded operations of the memory devices including program and erase operations. In the present device, the memory devices include a flash memory device (not shown in FIGS. 1 and 2) that stores sensed data and/or data pertaining to functionality of IMD 10 such as operating parameters, commands, and instructions.

Figure 3:
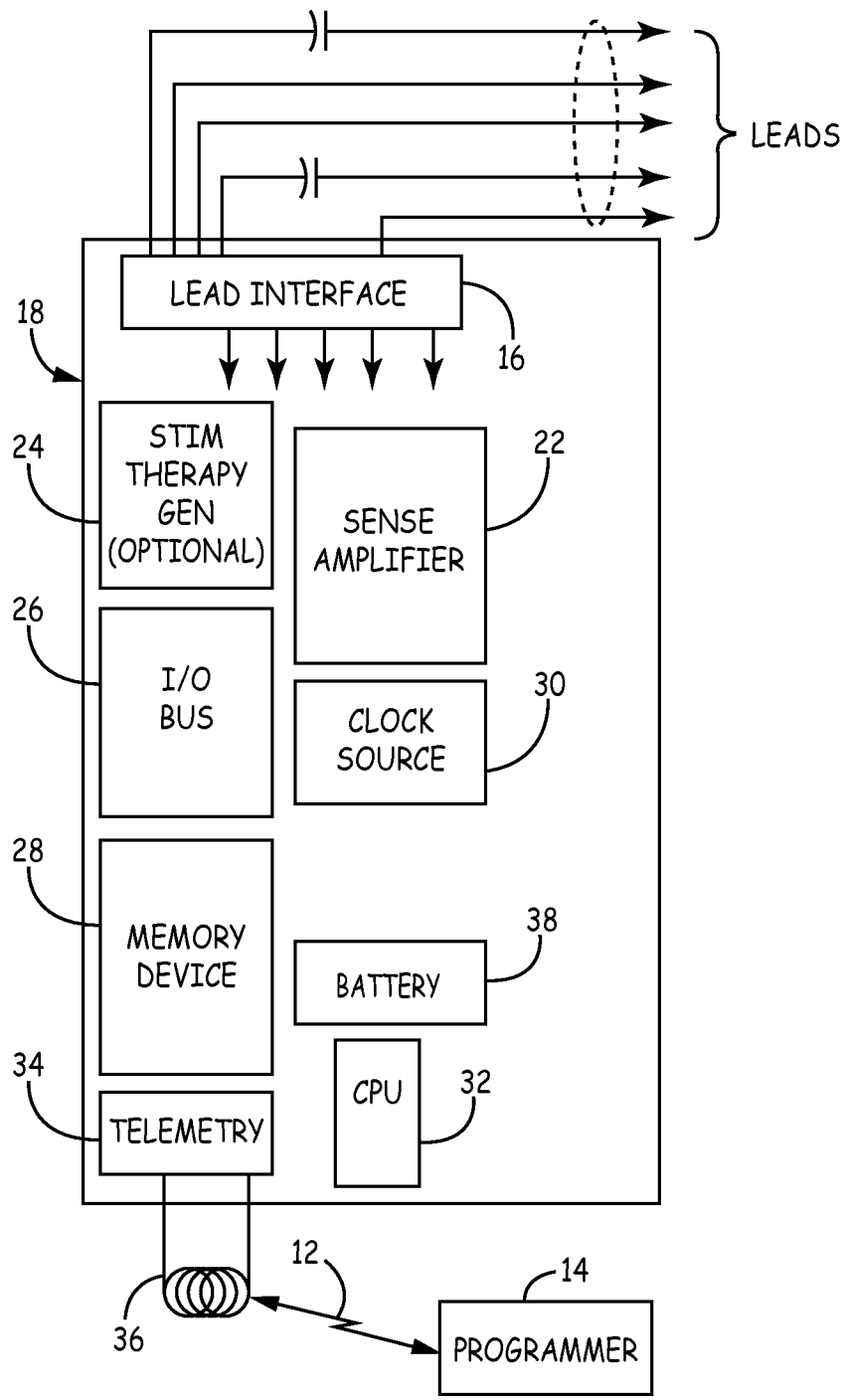
FIG. 3 is a block diagram of an embodiment of operational circuitry that may be utilized within the implantable medical devices of FIGS. 1 and 2 in accordance with embodiments of the present disclosure.

FIG. 3 is a block diagram of an embodiment of operational circuit 18 that may be utilized within miniaturized devices such as IMD 10 in accordance with the present disclosure. It is common to provide circuitry in the IMD 10 for achieving a variety of functionality to control therapy delivery and sensing functions. Portions of operational circuit 18 may be of conventional design such as disclosed in U.S. Pat. No. 5,052,388 issued to Sivula et al. For example, operational circuit 18 may include sense amplifier circuitry 22, an optional electrical stimulating generator 24, an input/output (I/O) Bus 26, and a random-access and/or read-only memory (RAM/ROM) device 28.

Operational circuit 18 includes a clock unit 30. The clock unit 30 provides clock signals of one (or a plurality of differing) frequencies as desired for operation of the various segments of operational circuit 18. In one example, the clock unit 30 may include a high accuracy oscillator such as a crystal oscillator that provides signals for calibrating various low-power clocks. The single calibrating source, high accuracy oscillator, coupled with several low-power clocks may be provided to reduce the current consumption of the operation circuitry 18.

The present invention provides additional techniques for optimizing power consumption of implantable medical devices, such as IMD 10.

A central processing unit (CPU) 32 is also provided for executing instructions stored in memory, including memory device 28, to cause IMD 10 to perform various functions attributed to the IMD 10. Such functions include controlling sense amplifier circuitry 22 to monitor/sense signals associated with the electrical activity of the heart 4, and/or causing stimulating therapy generator 24 to deliver stimulation therapy in the form of pacing pulses or defibrillation to heart 4 according to operational parameters or programs, which may also be stored in memory device 28.

CPU 32 is provided to control operations of the memory device 28 and to send addresses for manipulation of data in memory device 28. The operations of the memory device 28 may include such things as erasing and programming data. In one embodiment, the CPU 32 may determine a location within the memory device 28 at which data is to be stored (programmed). The CPU 32 may also determine a location within the memory device 28 at which data is to be retrieved (read). As will be described in more detail below, the CPU 32 sends appropriate instructions/commands to initiate an operation by memory device 28 based on a desired functionality of IMD 10. For example, the functionality may involve acquiring physiological signals from patient 2. Without intending to be limiting, the IMD 10 will sense the physiological signals through an electrode/electrode pair, transmit the sensed signals to the CPU 32 for processing, send the results of the processing to the memory device 28 for storage and/or send the raw sensed signals to the memory device 28 for storage. CPU 32 can be any of a variety of suitable controller devices, including microprocessors, application specific integrated circuits (ASICs), or other circuits or controllers.

A communications unit such as telemetry system 34 may be provided to allow the device to communicate with external devices such as programmer 14 and other devices via antenna 36 along communication channel 12. Examples of communication techniques may include, for example, low frequency or radiofrequency (RF) telemetry, but other techniques are also contemplated. In some embodiments, the IMD 10 receives telemetered signals that may include data, instructions, and/or commands that may alter one or more functions or operations of the IMD 10. One such function pertains to the storage and retrieval of information from the memory device 28, as will be described in more detail below.

In alternative embodiments, additional exemplary electrical components that may be included in the operational circuit 18 are further described in the circuit of the device(s) in U.S. Pat. No. 5,987,352, "Minimally Invasive Implantable Device for Monitoring Physiologic Events" to Klein et al., incorporated herein by reference in its entirety.

The operational circuit 18 may be powered by a finite-capacity power source such as battery 38. The battery 38 may be rechargeable, but in most implantable medical devices, such as IMD 10, may be non-rechargeable. As a result, one design constraint that was considered by the inventors of the present invention is ensuring that the functions of the IMD 10 are optimized to facilitate the fulfillment of the power supply demands from each component of the operational circuit 18. In particular, the inventors have addressed challenges associated with the reduced footprint, and hence storage capacity, of the battery 38 in meeting the peak power supply demands of high current operations. Those high current operations include the erase/program operations associated with the memory device 28.

Figure 4:
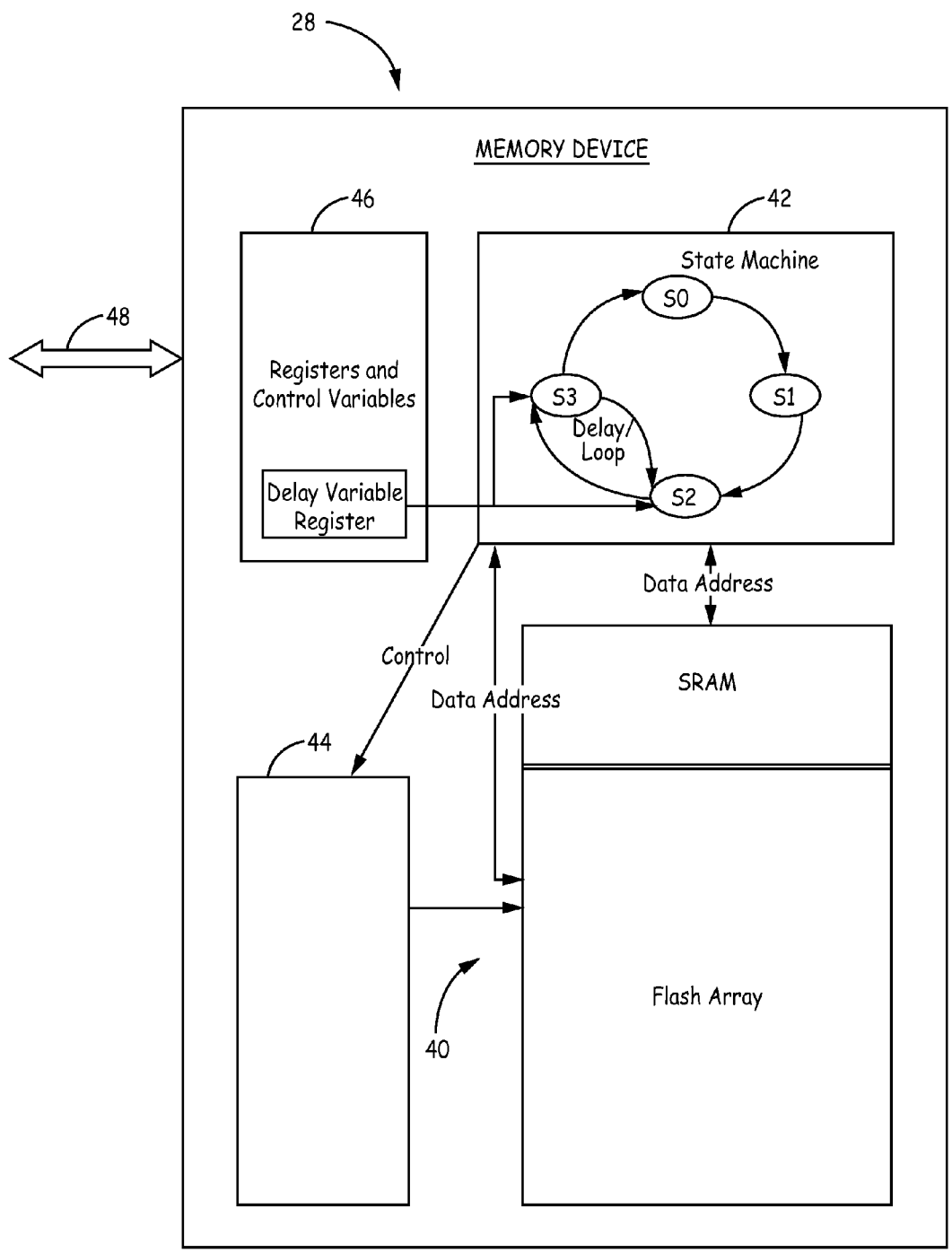
FIG. 4 provides a block diagram of one embodiment of a memory device of an implantable medical device of the present disclosure.

FIG. 4 provides a block diagram of one embodiment of memory device 28. The memory device 28 associated with IMD 10 may refer to one or more types of memory associated with implantable medical devices, including flash memory, random-access memory (RAM), read-only memory (ROM), electrically erasable programmable read-only memory (EEPROM), and a non-volatile random-access memory (NVRAM). For purposes of the present invention, the memory device 28 includes at least a flash memory array 40. In an embodiment, the flash memory array 40 may be include memory cells of a static RAM (SRAM) as is described in commonly owned and assigned U.S. patent application Ser. No. 13/663,099, "MEMORY ARRAY WITH FLASH AND RANDOM ACCESS MEMORY AND METHOD THEREFOR" to Walsh et al. The memory device 28 is functionally coupled to various components of the operational circuit 18 through a system bus 48.

In one implementation, the memory device 28 includes a state machine 42 for executing commands/instructions, (pre-determined) simple commands (or command sequences), from the CPU 32 based on received data. Example simple commands facilitate operations including, read, write, copy, erase, and so forth, of data residing in the flash memory array 40 and/or data received for storage in the memory device 28. In alternative embodiments, the functions attributed to state machine 42 may be performed directly by CPU 32 or a microcontroller, co-processor, microprocessor (or any combination of a microcontroller, co-processor, microprocessor, or state machine) that are within or located external to the memory device 28. In one implementation, a portion of the memory device 28 may be utilized for storage of data and program instructions (i.e., code) used to implement operations of the state machine 42 for manipulation or modification of the flash memory array 40.

Briefly, when the CPU 32 wants to access the flash memory array 40, it may send a request containing the targeted data address to the state machine 42. The state machine 42 then sends the proper commands to the segment, element, or sector of flash memory array 40 to perform the requested memory access operation. The commands may cause erasure of the sector and then rewriting of the new data into the sector. During a data write, the full flash memory may be erased and rewritten, a memory sector may be erased and rewritten, a memory element may be erased and rewritten, or a memory segment may be erased and rewritten—depending upon the flash architecture. In the example embodiments below, a sector erase and write will be used to illustrate the embodiment.

Charge pumps 44 are included in the memory device 28 and are regulated to provide voltage signals to the flash memory array 40. These voltage signals control particular voltages needed during embedded operations of the flash memory array 40. For example, the cell gate voltage during a program operation, the cell source or bulk voltage during an erase operation, and the cell gate voltage during a verify operation are provided by the charge pumps 44. Control signals for regulating the voltage signals from the charge pumps 44 may be generated by the state machine 42 or a processor located externally to the memory device 28.

Memory device 28 further includes one or more register bank(s) 46 (collectively "register 46") that are used to control parameters of the embedded operations of flash memory array 40. The operations are controlled according to configuration values that are loaded into the register 46 and which are appropriate to a particular current phase of the state machine 42 for a given flash memory operation. Each register 46 is therefore associated with a particular design parameter that is used in an ongoing operation of the memory device 28. For example, a register can be associated with a parameter that is an analog device signal (a voltage or current), or registers can be used to configure various parameters associated with the read, write (program), or erase operations of the flash memory array 40. Each design parameter may have two or more values that are stored within a corresponding two or more of the registers in register 46. The values of the parameters may be predetermined and pre-coded into the registers, or dynamically provided by the CPU 32 as a function of one or more operations of the CPU 32. In use, the state machine 42 accesses and loads the configuration values associated with one or more of the parameters, which are stored in the register 46, to implement operations of the state machine 42 for manipulation or modification of data in the flash memory array 40.

In accordance with the present disclosure, the register 46 may be implemented to store multiple configuration values associated with a conditional delay parameter for implementing the state machine 42. The multiple configuration values may have different values such that each of the values is associated with a different timing when implemented by the state machine 42. For example, a plurality of the timing values may be stored in register 46, each of the values being associated with a duration parameter. The multiple values of the duration parameter may be different and are associated with a conditional delay of an operation of the flash memory array 40. For example, the conditional delay may be a programming delay of a programming operation of the flash memory array 40. Although not shown in FIG. 4, a number of multiplexers may be provided in the memory device 28. At the inputs of each multiplexer are the individual registers associated with a given parameter, which contain the different configuration values pertinent to the particular parameter. The multiplexers may be used to select one of the inputs to the multiplexer to pass a configuration value through to the output of the multiplexer.

In one implementation, the state machine 42 receives instructions from CPU 32 for performing an operation such as accessing a location of the flash memory array 40 to store or retrieve data, for example. Such instructions to the state machine 42 may include the address or location within the memory array 40 to be accessed and the memory device operation to be performed. Receipt of the instructions from CPU 32 initializes the launch of the state machine 42 to perform the required operation. Consequently, the state machine 42 issues commands to control the charge pump 44 and to load values associated with the control parameters for fulfilling the required operation.

In accordance with the present invention, one such control parameter is the programming delay associated with programming data into the flash memory array 40. An appropriate programming delay value is loaded into the state machine 42 from the register 46 to enable the operation of programming of data.

The selection of a programming delay value during a given programming operation may be based on predetermined criteria. The criteria for selection of the programming delay value may include parameters associated with the battery 38. For example, the parameters may include a remaining energy stored in the battery (battery capacity), an effective impedance of the battery, a peak-demand current output, or any other desired current battery performance indicator. In accordance with the present invention, each programming delay value is associated with a calculated parameter of the battery. The use of the remaining battery energy as the control parameter may be of particular interest with respect to high current operations—during which, it is desirable to ensure that the battery can supply predetermined levels of peak current to the circuit. In the example of the parameter being the battery capacity, one or more programming delay values may be provided to modify the programming operation based on the remaining energy stored by the battery. The programming delay values are defined to provide sufficient time for the battery 38 (and other associated power supply components such as capacitors) to recover after each programming operation as will be discussed with reference to FIG. 5.

In an exemplary implementation, the individual ones of register 46 may each be loaded with a different programming delay value. For example, the values may range from 1.0 microsecond (µs) to 400 µs, although it should be understood that other values outside of this range may be utilized. In any event, the selection of one of those values (within or outside the range) may be based on a (delay) duration that enables the battery 38 to recover sufficiently to meet the current demands (peak or otherwise) for all concurrently-running operations of IMD 10 that are to be powered by the battery 38 at a given time.

In the description of the aforementioned embodiment of FIG. 4, the programming delay value has been described as being calculated with each requested memory access operation (programming, erasing etc.). However, it should be understood that in various other implementations, the programming delay value may be calculated at other intervals. For example, alternative embodiments may calculate the programming delay value at the beginning of the battery life with the value being used throughout the entire device operation, or the programming delay value may be calculated (once or multiple value) in response to the remaining battery energy reaching a predetermined value, or any other desired interval during the operating life of the battery.

Figure 5:
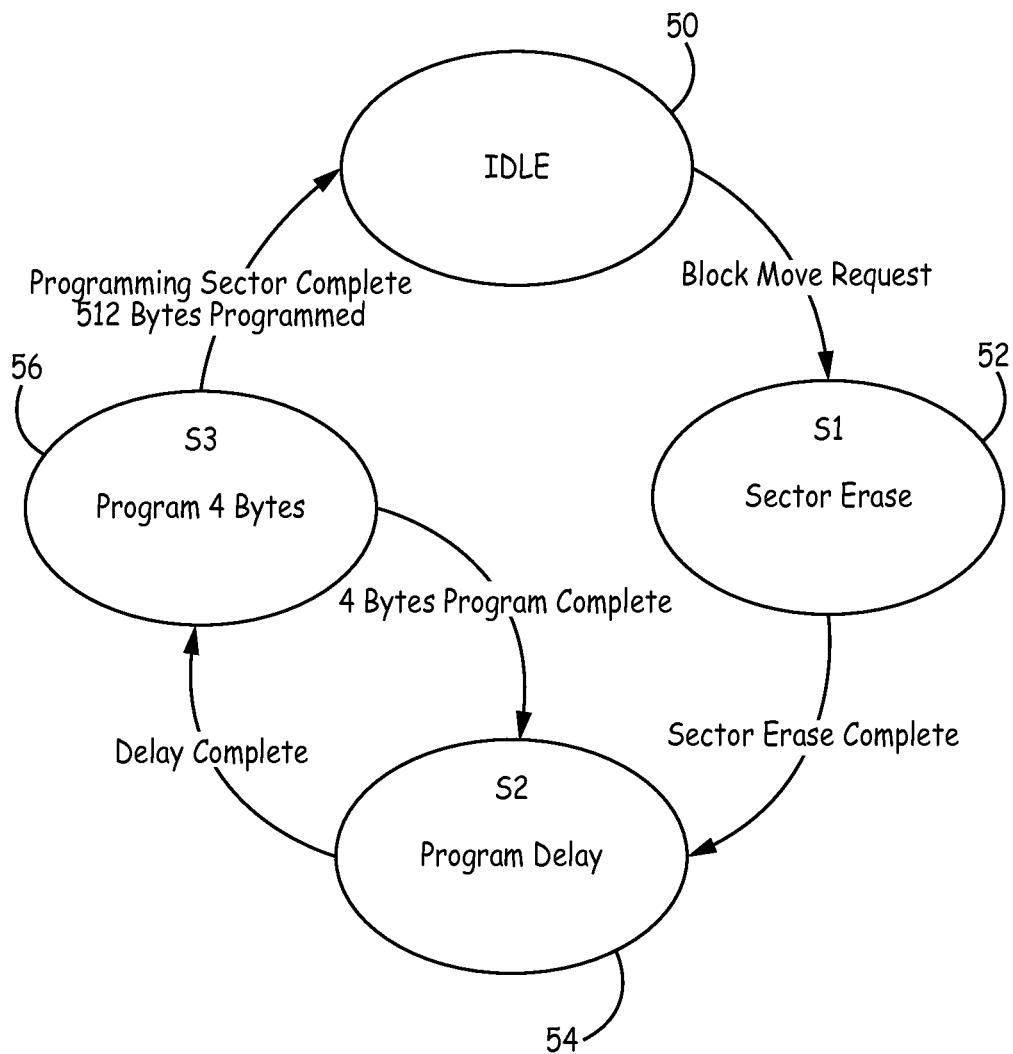
FIG. 5 depicts a graph representing an embodiment of the state machine of the memory devices of the present disclosure.

Turning to FIG. 5, a graph representing an embodiment of the state machine 42 of FIG. 4 is illustrated. The operation depicted in the state machine 42 is that of programming data into a memory location of the flash memory array 40 as a function of the values for various control parameters supplied by register 46 (including a programming delay) and external signals from the CPU 32. Nevertheless, this depiction is not intended to be limiting of the operations performed by the state machine 42. Rather, it should be understood that the state machine 42 may suitably be configured to control other operations of the flash memory array 40 such as reading or merely erasing data. The state machine 42 may be implemented in the form of a logic network of any known type. In the illustrated embodiment, the state machine includes four states indicated as S0, S1, S2, and IDLE (i.e., deactivated). Each of the states generally corresponds to a given operation of the memory device 28. The state machine 42 is configured to change states as a function of an internal timer and/or as a function of external events suitably synchronized.

In the illustrated embodiment, the state machine 42 is initialized by an external event (e.g., command or signal) received from CPU 32. For simplicity, the external event will be referred to herein as a PROGRAM command. The PROGRAM command instructs state machine 42 to store data in the flash memory array 40.

In response to receipt of the PROGRAM command from the CPU 32, the state machine 42 extracts the parameters stored in register 46 that are associated with the PROGRAM command. Initialization of the state machine by the PROGRAM command causes passage from the IDLE state 50 to state S0—erase operation 52. In accordance with an embodiment of the present invention, a sector of the flash memory array 40 comprises of 512 bytes. However, it should be appreciated that the sector may be configured having any other size and number of bytes that may be smaller, e.g., 256 bytes or larger, e.g., 4 Kbytes. In the implementation of a NOR flash memory array, the entire sector is erased before data is written.

At S2, the state machine implements a program delay 54 between the writing of data to each memory element. The memory element refers to a constituent unit of the memory sectors of flash memory array 40. In other words, each memory sector may comprise two or more memory elements that can be written to individually. In one implementation, a sector of the flash memory array 40 comprises 512 bytes and each sector comprises of 128 memory elements (i.e., each element is 4 bytes long). Further, it should be understood that the memory elements may comprise of even smaller units (memory segments) and so forth. Nevertheless, to avoid unnecessarily obfuscating the invention, the smallest divisible unit described herein will be the memory element.

At S3, a program operation 56 of data to the flash memory array 40 is performed by sequentially writing to each memory element in the sector. The programming 56 is performed in several iterations, with each of the iterations comprising writing the data to a first of the memory elements followed by a program delay 52 and then writing data to a second of the memory elements followed by another program delay 52 and so forth. In other words, the state machine 42 loops between states S2 and S3 during the programming operation 56 until completion of the writing to the memory elements in a given sector. As such, if the sector includes two memory elements, then only one programming delay will be introduced between the programming of the first and second elements, or if the sector includes three memory elements, then two programming delays will be injected and so forth. Thus, a programming loop is defined by the states S2 and S3.

As previously described, the value of the program delay 54 is determined based on a parameter of the battery 38. In the non-limiting example of the parameter being the capacity of the battery 38, the program delay value for the battery 38 at full capacity may be smaller relative to the program delay value for battery 38 at half capacity. For illustrative purposes, the program delay value for the battery at full capacity may be 1 µs, whereas the program delay value for the battery at half capacity is defined at 100 µs. Continuing with the illustrative example, the program delay value for the battery at a quarter capacity may be defined at 200 µs.

In other words, the program delay value will have a progressively increasing duration as the remaining capacity or remaining energy stored by the battery 38 decreases. The increase in the duration defined by the program delay value accounts for the inventors' recognition—that the battery and associated energy supply components require an increasing amount of time to recover operational power for supplying current demands as the battery capacity declines.

If the PROGRAM command is successfully executed, the state machine returns to state S0. Techniques for determining whether the PROGRAM command has been successfully executed are known and will not be discussed in detail herein. Suffice it to note that, any known error detection and correction schemes may be implemented to verify the accuracy of the data that is written to each segment, element and/or sector of the flash memory array.

The state machine is capable of "going through" all the states S0, S1, S2 and S3 (i.e. rotate in sequence through such states), as represented with the full line, as a function of the memory array functions and/or of external events. In various embodiments, the working parameters of the state machine can be varied by software means.

Figure 6A:
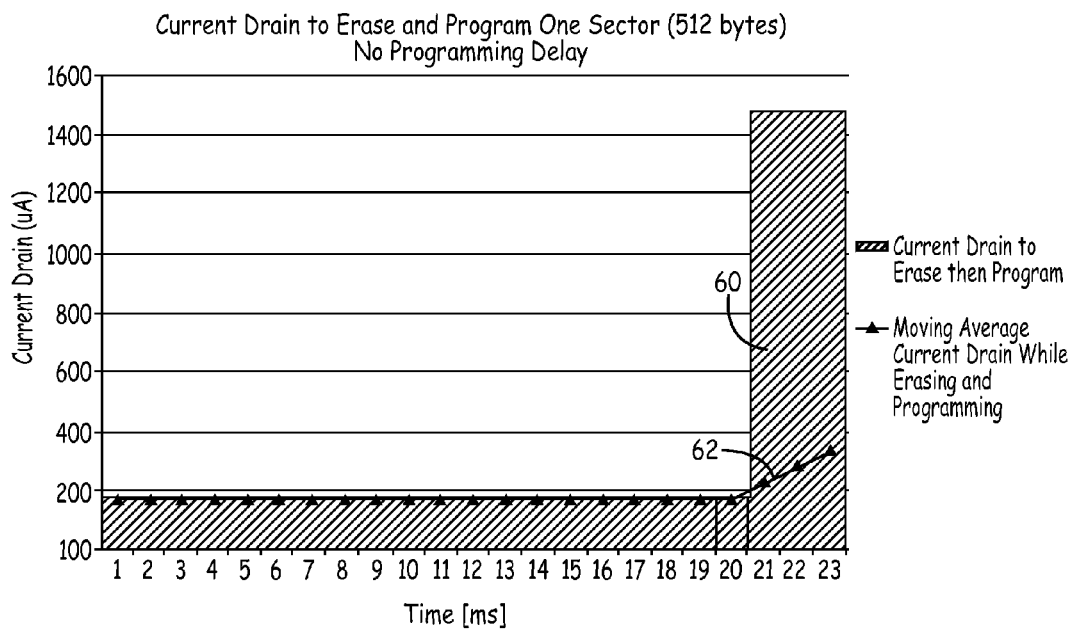
FIG. 6A shows a plot of the sector program time verses the cumulative current drain without implementing a program delay.

FIG. 6A shows a plot of program time for a memory sector versus the cumulative current drain without implementing a program delay. As discussed above, the program operation includes an erase that is followed by writing of data. In the program operation of FIG. 6A, the entire sector is written-to following an erase, without a program delay. As such, in the implementation of the state machine of FIG. 5, the sequence of states goes from S1 to S3 without the step of introducing a delay—i.e., no S2. This is akin to the conventional operation of the state machines of conventional flash memory arrays.

Figure 6B:
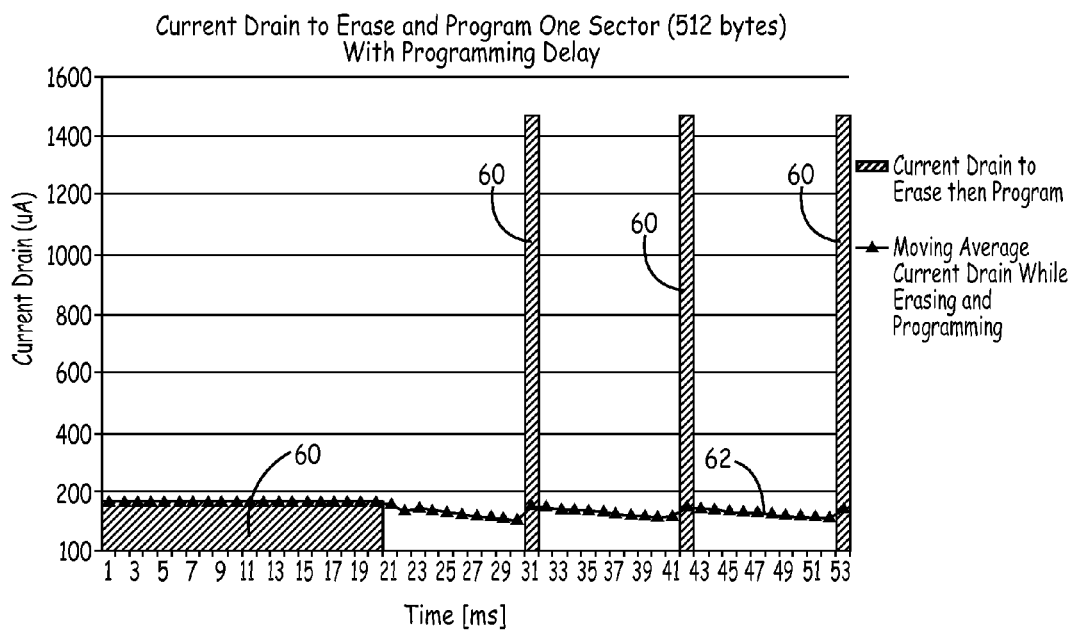
FIG. 6B shows a plot of the sector program time verses the cumulative current drain with a program delay that is selected based upon the capacity of the battery.

FIG. 6B shows a plot of the program time for a memory sector versus the cumulative current drain with a program delay that is selected based upon the capacity of the battery. By providing a delay between the program operations of the two or more memory elements of a sector, the battery 38 is afforded sufficient time to recover operational power to support the peak power demands. In the implementation of the program delay of FIG. 6B, the delay may cause the current drain during the program (writing) operation to be reduced to match the current drain during the erase operation.

In comparison to the plot of FIG. 6A, the duration of completion of the program operation in FIG. 6B is longer. The legend in the plots of FIGS. 6A and 6B (right-hand section) shows the amount of current drain to erase then program and the moving average current drain to erase and program full sector. Depending on the particular implementation, one benefit of providing a delay between the programming of the memory elements in a given sector is that the current drain associated with each programming operation is decreased. In one experimental comparison of the two implementations, the current drain associated with an implementation without a program delay was found to be about 800 μamps whereas the current drain associated with the implementation with a program delay was found to be about 180 μamps.

Accordingly, the techniques of the present disclosure facilitate miniaturization of devices, such as IMD 10, that are configured for implantation in a patient. In accordance with aspects of the present invention, implementing a memory device with a programming delay enables the downsizing of the battery size and capacity of an implantable medical device. The reduced form factor of the battery facilitates the miniaturization of the implantable medical devices. The memory devices of the present disclosure may include non-transitory computer readable storage media storing instructions that, when executed by one or more processing circuits, cause the modules to perform various functions attributed to IMD 10. The storage media may include any computer-readable storage media with the sole exception being a transitory, propagating signal.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. It should also be understood that various changes can be made in the function and arrangement of elements without departing from the scope of the disclosure as set forth in the appended claims and the legal equivalents thereof.

What is claimed is:

1. An implantable medical device comprising:
   a battery;
   a processing unit coupled to the battery;
   a memory device coupled to the processing unit having:
      a memory sector including a plurality of memory elements;
      a state machine configured to control a programming delay duration associated with a programming operation of the memory sector as a function of a parameter of the battery.

2. An implantable medical device comprising:
   a battery;
   a processing unit coupled to the battery;
   a memory device coupled to the processing unit having:
      a memory sector including a plurality of memory elements;
   a state machine configured to control a timing associated with a programming operation of the memory sector as a function of a parameter of the battery, wherein controlling the timing associated with the programming operation of the memory sector comprises controlling a timing of writing of data to a second memory element as a function of a programming delay duration following a preceding writing of data to a first memory element.

3. The implantable medical device of claim 2, wherein the programming delay duration is correlated to the parameter of the battery.

4. The implantable medical device of claim 2, wherein the programming delay value is defined as a function of a remaining amount of energy stored by the battery.

5. The implantable medical device of claim 1, wherein the state machine is further configured to perform an erasing operation of data in the memory sector prior to performing the programming operation.

6. The implantable medical device of claim 1, wherein the processing unit is configured to calculate the parameter of the battery.

7. The implantable medical device of claim 6, wherein the calculated parameter of the battery is a remaining amount of energy stored by the battery.

8. The implantable medical device of claim 1, wherein the state machine controls the programming operation by delaying the writing of data in a second memory element after writing data to a preceding one of the plurality of memory elements.

9. The implantable medical device of claim 8, further comprising a register configured to hold a programming delay value, wherein the programming delay value defines a duration of the delaying of the writing of data in the second memory element.

10. The implantable medical device of claim 1, wherein the state machine is further configured to control an erasing operation of the memory sector as a function of the parameter of the battery.

11. An implantable medical device, comprising:
a battery;
a processing unit coupled to the battery; and
a memory device coupled to the processing unit, including:
　a memory sector having a plurality of elements; and
　means for controlling a programming delay duration of a programming operation of the memory sector as a function of a parameter of the battery.

12. An implantable medical device, comprising:
a battery;
a processing unit coupled to the battery; and
a memory device coupled to the processing unit, including:
　a memory sector having a plurality of elements; and
　means for controlling a timing of a programming operation of the memory sector as a function of a parameter of the battery, wherein the means for controlling the programming operation of the memory sector applies a programming delay between the programming of each one of the plurality of memory sector elements.

13. The implantable medical device of claim 12, further comprising means for storing one or more values associated with a programming delay, wherein the programming delay is implemented by the means for controlling the timing.

14. The implantable medical device of claim 13, wherein the one or more values are associated with the parameter of the battery.

15. The implantable medical device of claim 14, wherein the parameter includes a remaining amount of energy stored by the battery.

16. An implantable medical device comprising:
a battery;
a processing unit coupled to the battery;
a memory device coupled to the processing unit having:
　a memory sector including a plurality of memory elements;
　a state machine configured to control a programming delay duration associated with a programming operation of the memory sector as a function of a remaining amount of energy stored by the battery, wherein controlling the programming delay duration associated with the programming operation of the memory sector comprises controlling the delay prior to writing of data to a first memory element.

17. The implantable medical device of claim 16, wherein controlling the programming delay duration associated with the programming operation of the memory sector comprises controlling the programming delay duration of writing of data to a second memory element as a function of a programming delay duration following the preceding writing of data to the first memory element.

* * * * *